United States Patent
Gauglitz et al.

(10) Patent No.: US 9,766,307 B2
(45) Date of Patent: *Sep. 19, 2017

(54) SYSTEMS AND METHODS FOR SENSING EXTERNAL MAGNETIC FIELDS IN IMPLANTABLE MEDICAL DEVICES

(71) Applicant: Cardiac Pacemakers, Inc., St. Paul, MN (US)

(72) Inventors: Karl Gauglitz, Snohomish, WA (US); Thomas M. Bocek, Seattle, WA (US); Mark Rutzer, Seattle, WA (US); Lorin W. Matthews, Brier, WA (US); William E. Reagor, Bellevue, WA (US); Blair Erbstoeszer, Kirkland, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 508 days.

This patent is subject to a terminal disclaimer.

(21) Appl. No.: 14/204,559

(22) Filed: Mar. 11, 2014

(65) Prior Publication Data

US 2014/0194729 A1    Jul. 10, 2014

Related U.S. Application Data

(63) Continuation of application No. 13/282,968, filed on Oct. 27, 2011, now Pat. No. 8,710,826, which is a
(Continued)

(51) Int. Cl.
*A61B 5/055*    (2006.01)
*A61N 1/36*    (2006.01)
(Continued)

(52) U.S. Cl.
CPC ............ *G01R 33/287* (2013.01); *A61B 5/055* (2013.01); *A61N 1/3605* (2013.01);
(Continued)

(58) Field of Classification Search
CPC .............. A61N 1/3718; A61N 1/13605; A61N 1/3956; G01V 3/101
See application file for complete search history.

(56) References Cited

U.S. PATENT DOCUMENTS

| 2,841,763 A | 7/1958 | Williams et al. |
| 2,980,846 A | 4/1961 | Ringelman |
| (Continued) | | |

FOREIGN PATENT DOCUMENTS

| GB | 2395276 A | 5/2004 |
| WO | WO-03037429 A1 | 5/2003 |

OTHER PUBLICATIONS

U.S. Appl. No. 11/460,081, Advisory Action, 3 pgs.
(Continued)

*Primary Examiner* — Sean Dougherty
(74) *Attorney, Agent, or Firm* — Schwegman Lundberg & Woessner, P.A.

(57) ABSTRACT

Systems and methods for sensing external magnetic fields in implantable medical devices are provided. One aspect of this disclosure relates to an apparatus for sensing magnetic fields. An apparatus embodiment includes a sensing circuit with at least one inductor having a magnetic core that saturates in the presence of a magnetic field having a prescribed flux density. The apparatus embodiment also includes an impedance measuring circuit connected to the sensing circuit. The impedance measuring circuit is adapted to measure impedance of the sensing circuit and to provide a signal when the impedance changes by a prescribed amount. According to an embodiment, the sensing circuit includes a resistor-inductor-capacitor (RLC) circuit. The impedance measuring circuit includes a transthoracic
(Continued)

impedance measurement module (TIMM), according to an embodiment. Other aspects and embodiments are provided herein.

19 Claims, 4 Drawing Sheets

Related U.S. Application Data continuation of application No. 11/460,081, filed on Jul. 26, 2006, now Pat. No. 8,049,489.

(51) Int. Cl.
    *A61N 1/39*     (2006.01)
    *G01R 33/28*     (2006.01)
    *A61N 1/37*     (2006.01)
    *G01V 3/10*     (2006.01)

(52) U.S. Cl.
    CPC ......... *A61N 1/3718* (2013.01); *A61N 1/3956* (2013.01); *G01V 3/101* (2013.01)

(56) References Cited

U.S. PATENT DOCUMENTS

| | | | |
|---|---|---|---|
| 3,968,802 A | 7/1976 | Ballis | |
| 4,357,943 A | 11/1982 | Thompson | |
| 4,541,431 A | 9/1985 | Ibrahim et al. | |
| 4,553,095 A | 11/1985 | Schenk et al. | |
| 4,745,923 A | 5/1988 | Winstrom | |
| 5,030,196 A | 7/1991 | Inoue | |
| 5,217,010 A | 6/1993 | Tsitlik et al. | |
| 5,351,004 A | 9/1994 | Daniels et al. | |
| 5,481,238 A | 1/1996 | Carsten et al. | |
| 5,612,862 A | 3/1997 | Marusik et al. | |
| 5,697,958 A | 12/1997 | Paul et al. | |
| 5,759,197 A | 6/1998 | Sawchuk et al. | |
| 6,100,680 A | 8/2000 | Vig et al. | |
| 6,101,417 A | 8/2000 | Vogel et al. | |
| 6,209,764 B1 | 4/2001 | Hartlaub et al. | |
| 6,414,835 B1 | 7/2002 | Wolf et al. | |
| 6,424,145 B1 | 7/2002 | Woolsey et al. | |
| 6,507,189 B2 | 1/2003 | Woolsey et al. | |
| 6,522,920 B2 | 2/2003 | Silvian et al. | |
| 6,564,084 B2 | 5/2003 | Allred, III et al. | |
| 6,741,885 B1* | 5/2004 | Bornzin | A61N 1/3627 |
| | | | 600/509 |
| 6,795,730 B2 | 9/2004 | Connelly et al. | |
| 6,930,242 B1* | 8/2005 | Helfer | B82Y 25/00 |
| | | | 174/102 SC |
| 6,963,779 B1 | 11/2005 | Shankar | |
| 6,971,391 B1 | 12/2005 | Wang et al. | |
| 7,068,030 B2 | 6/2006 | Hintz et al. | |
| 7,076,283 B2 | 7/2006 | Cho et al. | |
| 7,091,412 B2 | 8/2006 | Wang et al. | |
| 7,127,294 B1 | 10/2006 | Wang et al. | |
| 7,151,963 B2 | 12/2006 | Havel et al. | |
| 7,164,950 B2 | 1/2007 | Kroll et al. | |
| 7,295,107 B2 | 11/2007 | Massengill et al. | |
| 7,729,770 B2 | 6/2010 | Cabelka et al. | |
| 7,765,005 B2 | 7/2010 | Stevenson | |
| 7,792,572 B1* | 9/2010 | Gill | A61B 5/0452 |
| | | | 128/920 |
| 8,049,489 B2 | 11/2011 | Gauglitz et al. | |
| 2001/0019262 A1 | 9/2001 | Woolsey et al. | |
| 2002/0123682 A1 | 9/2002 | Allred, III et al. | |
| 2003/0078493 A1 | 4/2003 | Ogawa et al. | |
| 2003/0140931 A1 | 7/2003 | Zeijlemaker et al. | |
| 2003/0144704 A1 | 7/2003 | Terry et al. | |
| 2003/0144705 A1 | 7/2003 | Funke | |
| 2004/0017191 A1 | 1/2004 | Stanley | |
| 2004/0046536 A1 | 3/2004 | Librizzi | |
| 2004/0135687 A1 | 7/2004 | Keene | |
| 2004/0139975 A1* | 7/2004 | Nelson | A61F 2/00 |
| | | | 128/848 |
| 2004/0210289 A1 | 10/2004 | Wang et al. | |
| 2004/0230271 A1* | 11/2004 | Wang | A61M 25/0045 |
| | | | 607/116 |
| 2004/0263173 A1 | 12/2004 | Gray | |
| 2004/0267233 A1 | 12/2004 | Ginggen | |
| 2005/0004417 A1 | 1/2005 | Nelson et al. | |
| 2005/0070787 A1* | 3/2005 | Zeijlemaker | A61N 1/3718 |
| | | | 600/411 |
| 2005/0079132 A1 | 4/2005 | Wang et al. | |
| 2005/0197677 A1 | 9/2005 | Stevenson | |
| 2005/0242804 A1 | 11/2005 | Hintz et al. | |
| 2006/0145691 A1 | 7/2006 | Massengill et al. | |
| 2006/0158331 A1 | 7/2006 | Massengill et al. | |
| 2006/0173295 A1* | 8/2006 | Zeijlemaker | A61N 1/37 |
| | | | 600/427 |
| 2006/0264730 A1 | 11/2006 | Stivoric et al. | |
| 2007/0080767 A1 | 4/2007 | Kuzmenka | |
| 2007/0083244 A1 | 4/2007 | Stevenson et al. | |
| 2007/0150022 A1* | 6/2007 | Ujhazy | A61B 5/0538 |
| | | | 607/42 |
| 2007/0191914 A1 | 8/2007 | Stessman | |
| 2008/0071168 A1 | 3/2008 | Gauglitz et al. | |
| 2012/0046707 A1 | 2/2012 | Gauglitz et al. | |

OTHER PUBLICATIONS

U.S. Appl. No. 11/460,081, Advisory Action mailed May 19, 2010, 3 pgs.
U.S. Appl. No. 11/460,081, Final Office Action mailed Jun. 22, 2010, 13 pgs.
U.S. Appl. No. 11/460,081, Final Office Action mailed Feb. 8, 2010, 13 pgs.
U.S. Appl. No. 11/460,081, Non Final Office Action mailed Jan. 21, 2011, 9 pgs.
U.S. Appl. No. 11/460,081, Non-Final Office Action mailed Jan. 12, 2009, 9 pgs.
U.S. Appl. No. 11/460,081, Non-Final Office Action mailed Aug. 20, 2009, 12 Pgs.
U.S. Appl. No. 11/460,081, Notice of Allowance mailed Jul. 19, 2011, 11 pgs.
U.S. Appl. No. 11/460,081, Response filed Apr. 27, 2009 to Non Final Office Action mailed Jan. 12, 2009, 9 pgs.
U.S. Appl. No. 11/460,081, Response filed Sep. 21, 2010 to Final Office Action mailed Jun. 22, 2010, 9 pgs.
U.S. Appl. No. 11/460,081, Response filed Oct. 17, 2008 to Restriction Requirement mailed Sep. 26, 2008, 5 pgs.
U.S. Appl. No. 11/460,081, Response filed Nov. 20, 2009 to Non Final Office Action mailed Aug. 20, 2009, 9 pgs.
U.S. Appl. No. 11/460,081, Response filed Apr. 18, 2011 to Non Final Office Action mailed Jan. 21, 2011, 12 pgs.
U.S. Appl. No. 11/460,081, Response filed May 10, 2010 to Final Office Action mailed Feb. 8, 2010, 8 pgs.
U.S. Appl. No. 11/460,081, Restriction Requirement mailed Sep. 26, 2008, 6 pgs.
U.S. Appl. No. 13/282,968, Response filed Jul. 1, 2013 to Final Office Action mailed May 2, 2013, 7 pgs.
U.S. Appl. No. 13/282,968, Final Office Action mailed May 2, 2013, 7 pgs.
U.S. Appl. No. 13/282,968, Non Final Office Action mailed Jul. 18, 2013, 6 pgs.
U.S. Appl. No. 13/282,968, Non Final Office Action mailed Nov. 20, 2012, 9 pgs.
U.S. Appl. No. 13/282,968, Notice of Allowance mailed Dec. 9, 2013, 10 pgs.
U.S. Appl. No. 13/282,968, Response filed Feb. 20, 2013 to Non Final Office Action mailed Nov. 20, 2012, 7 pgs.
U.S. Appl. No. 13/282,968, Response filed Oct. 8, 2013 to Non Final Office Action mailed Jul. 18, 2013, 5 pgs.
U.S. Appl. No. 13/282,968, Response filed Sep. 26, 2012 to Restriction Requirement mailed Sep. 5, 2012, Response to Restriction Requirement, 7 pgs.

(56) References Cited

OTHER PUBLICATIONS

U.S. Appl. No. 13/282,968, Restriction Requirement mailed Sep. 5, 2012, 6 pgs.

* cited by examiner

SYSTEMS AND METHODS FOR SENSING EXTERNAL MAGNETIC FIELDS IN IMPLANTABLE MEDICAL DEVICES

CLAIM OF PRIORITY

This application is a continuation of and claims the benefit of priority under 35 U.S.C. §120 to U.S. patent application Ser. No. 13/282,968, filed on Oct. 27, 2011, which is a continuation of and claims the benefit of priority under 35 U.S.C. §120 to U.S. patent application Ser. No. 11/460,081, filed on Jul. 26, 2006, now issued as U.S. Pat. No. 8,049,489, which is hereby incorporated by reference herein in its entirety.

TECHNICAL FIELD

This disclosure relates to implantable medical devices, particularly systems and methods for sensing external magnetic fields in implantable medical devices.

BACKGROUND

Implantable medical devices (IMDs) include devices such as implantable defibrillators, cardioverters, neurostimulators, and pacemakers. Since the early 1980s, thousands of patients prone to irregular and sometimes life threatening heart rhythms have had IMDs implanted in their bodies, typically in the upper chest area above their hearts. Certain of these devices detect onset of abnormal heart rhythms and automatically apply corrective electrical therapy, specifically one or more bursts of electric energy, to hearts. When the bursts of electric current are of sufficient amplitude and are properly synchronized with the cardiac signal, they restore normal heart function without human intervention, sparing patients considerable discomfort and often saving their lives.

With the increase in use of magnetic resonance imaging (MRI) as a diagnostic tool, patients with IMDs are exposed to strong magnetic fields on a more frequent basis.

SUMMARY

Disclosed herein, among other things, is an apparatus for sensing magnetic fields. An apparatus embodiment includes a sensing circuit with at least one inductor having a magnetic core that saturates in the presence of a magnetic field having a prescribed flux density. The apparatus embodiment also includes an impedance measuring circuit connected to the sensing circuit. The impedance measuring circuit is adapted to measure impedance of the sensing circuit and to provide a signal when the impedance changes by a prescribed amount.

An apparatus embodiment includes means for sensing the presence of a magnetic field from a magnetic resonance imaging device. This apparatus embodiment also includes means for measuring impedance connected to the sensing means, including means for signaling when the measured impedance changes by a prescribed amount. The means for sensing includes a resistor-inductor-capacitor (RLC) circuit, according to various embodiments. According to an embodiment, the means for measuring includes a transthoracic impedance measurement module (TIMM).

One aspect of this disclosure relates to an implantable medical device with magnetic field sensing capability. The device embodiment includes a sensing circuit with at least one inductor having a magnetic core that saturates in the presence of a magnetic field having a prescribed flux density. The device embodiment also includes an impedance measuring circuit connected to the sensing circuit. The impedance measuring circuit is adapted to measure the impedance of the sensing circuit and to provide a signal when the impedance changes by a prescribed amount. The device embodiment further includes a controller adapted to receive the signal and modify device behavior while in the presence of the magnetic field.

One aspect of this disclosure relates to a method for sensing external magnetic fields. The method embodiment includes sensing a magnetic field using a circuit having an inductor with a magnetic core that saturates in the presence of a magnetic field having a prescribed flux density, measuring impedance of the circuit, and sending a signal to an implantable medical device when the measured impedance indicates the inductor is saturated.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. These embodiments are described in sufficient detail to enable those skilled in the art to practice the invention. Other embodiments may be utilized and structural, logical, and electrical changes may be made without departing from the scope of the present invention.

System for Sensing External Magnetic Fields

Figure 1:
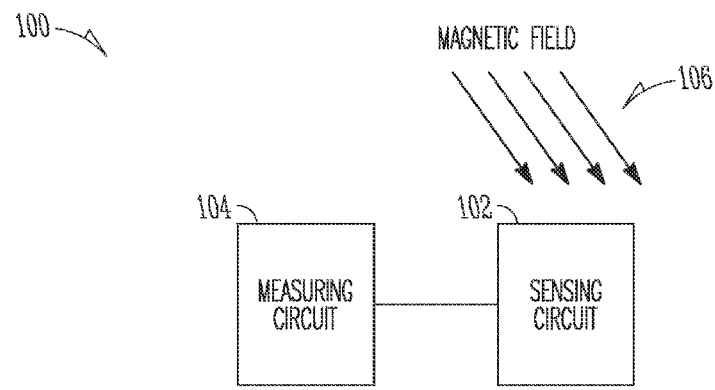
FIG. 1 illustrates a block diagram of a system for sensing magnetic fields, according to one embodiment.

FIG. 1 illustrates a block diagram of a system for sensing magnetic fields, according to one embodiment. The depicted apparatus 100 includes a sensing circuit 102 connected to an impedance measuring circuit 104. The sensing circuit 102 has at least one inductor having a magnetic core that saturates in the presence of a magnetic field 106 having a prescribed flux density. The impedance measuring circuit 104 is adapted to measure impedance of the sensing circuit and to provide a signal when the impedance changes by a prescribed amount. According to various embodiments, the impedance measuring circuit includes a transthoracic impedance measurement module (TIMM). The impedance measuring circuit delivers a current pulse to the sensing circuit to measure impedance, according to various embodiments. According to one embodiment, the impedance measuring circuit delivers a current pulse to the sensing circuit periodically.

According to various embodiments, the sensing circuit includes a resistor-inductor-capacitor (RLC) circuit. The impedance of the inductor changes upon saturation of the magnetic core, which changes the impedance of the RLC circuit containing the inductor. The impedance measuring circuit provides the signal to an implantable medical device, and the device modifies a behavior after receiving the signal, in various embodiments. Modifying device behavior may include changing to a pacing mode, changing to a tachy mode, changing lead configuration, or changing to a protect mode, according to various embodiments. Other types of device behavior or characteristics may be changed or modified upon receipt of the signal without departing from the scope of this disclosure.

According to an embodiment, the inductor or inductors include a ferrite drum core inductor. Other types of inductors can be used. Examples include, but are not limited to: gapped toroidal inductors or tape wound core inductors. According to various embodiments, the inductor or inductors include an isotropic material, so that the inductor(s) saturate as a result of magnetic field intensity only, independent of direction. According to various embodiments, the inductor is sized to fit within the housing of an implantable medical device. The inductor has maximum dimensions of 0.4 inches in width, 0.4 inches in length and 0.3 inches in height, according to one embodiment.

An apparatus embodiment includes means for sensing the presence of a magnetic field from a magnetic resonance imaging device. This apparatus embodiment also includes means for measuring impedance connected to the sensing means, including means for signaling when the measured impedance changes by a prescribed amount. The means for sensing includes a resistor-inductor-capacitor (RLC) circuit, according to various embodiments. According to an embodiment, the means for measuring includes a transthoracic impedance measurement module (TIMM). According to various embodiments, the means for sensing includes an inductor having a magnetic core that saturates at a selected magnetic flux density. The selected magnetic flux density includes a flux density of a Magnetic Resonance Imaging (MRI) machine, in an embodiment. The prescribed amount of impedance change includes a difference in impedance caused by saturation of the magnetic core, in various embodiments. The means for sensing includes an RLC circuit in an embodiment. Other types of sensing circuits having inductive elements capable of impedance changes at a prescribed flux density can be used. The means for measuring includes a TIMM in various embodiments. Other types of circuits able to measure impedance or detect a parameter indicative of impedance can be used without departing from the scope of this disclosure. According to various embodiments, detecting a parameter indicative of impedance includes detecting phase shift. The saturable magnetics described need not be a single inductor, but may include multiple inductors in a variety of orientations. The means for measuring can include a controller in various embodiments.

Figure 2:
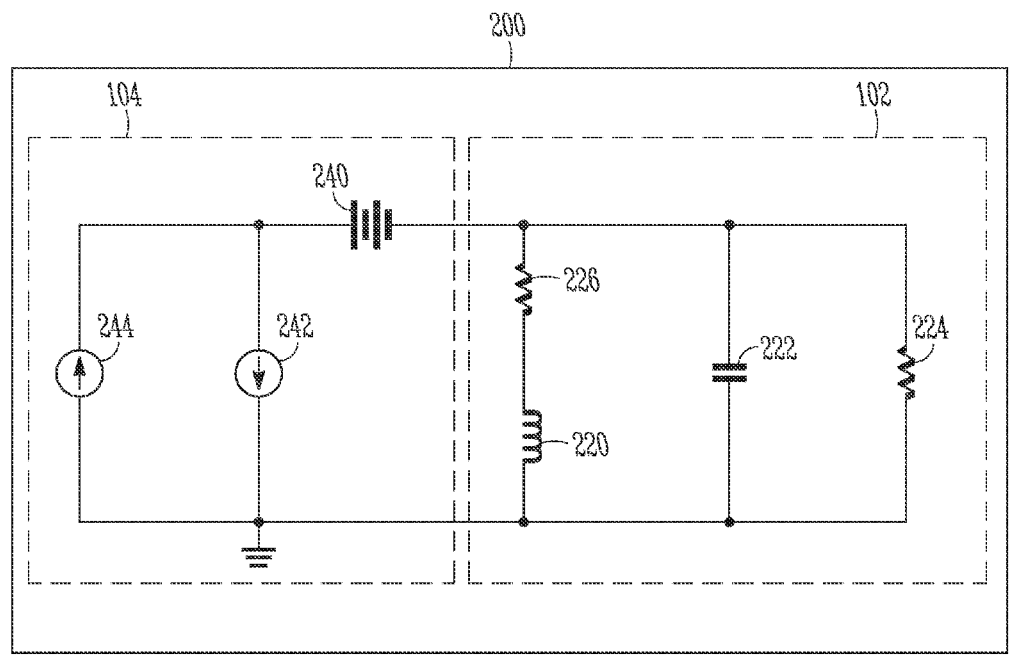
FIG. 2 illustrates a schematic diagram of a system for sensing magnetic fields, according to one embodiment.

FIG. 2 illustrates a schematic diagram of a system for sensing magnetic fields, according to one embodiment. The depicted apparatus 200 includes a sensing circuit 102 connected to an impedance measuring circuit 104. The sensing circuit 102 has at least one inductor 220 having a magnetic core that saturates in the presence of a magnetic field having a prescribed flux density. The impedance measuring circuit 104 is adapted to measure impedance of the sensing circuit and to provide a signal when the impedance changes by a prescribed amount.

According to various embodiments, the impedance measuring circuit 104 includes a transthoracic impedance measurement module (TIMM). The TIMM includes at least one voltage source 240 and a first current source 244 and second current source 242. The two current sources depicted in the figure are not essential, and a single source can by used so long as the source can provide both positive and negative current pulses to the sensor circuit. According to various embodiments, the sensing circuit includes a resistor-inductor-capacitor (RLC) circuit. In the depicted embodiment, the resistor 224, the capacitor 222 and the inductor 220 are connected in parallel. Other types of circuits, including series RLC circuits, can be used without departing from the scope of this disclosure. A second resistor 226 is shown in series with the inductor 220.

Saturable Magnetics

As discussed in FIG. 1 above, a system is provided for sensing magnetic fields using saturable magnetics. Saturable magnetics refers to the properties of a magnetic core around which the inductive coil is wound. The magnetic core will saturate when in the presence of a magnetic field with a strength (or flux density) at the level which causes all of the magnetic moments in the core material to line up with the applied magnetizing force. If an inductor has a saturated core, no further magnetic flux will result from further increases in current, and so there will be no voltage induced in opposition to the change in current. Thus, an inductor loses its inductance, or ability to oppose changes in current, when its core becomes magnetically saturated. If an inductor's inductance changes, then its reactance (and impedance) to AC current changes as well.

Figure 3:
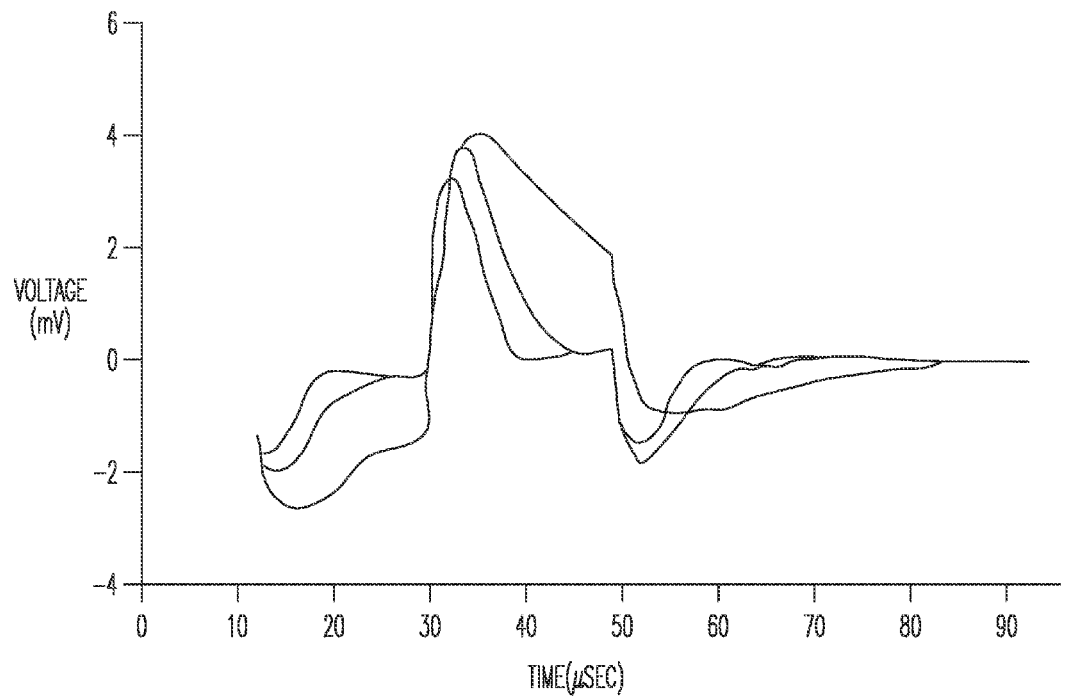
FIG. 3 illustrates a graphical diagram of measured impedance in a system for sensing magnetic fields, according to one embodiment.

As stated above, the inductor is selected with a magnetic core that saturates at a prescribed flux density. The flux density is chosen to cause saturation in the presence of a chosen magnetic field (such as that of an MRI device). Once this flux density is reached, the inductance, and therefore the impedance, of the sensor circuit drops dramatically. The measurement circuit measures the impedance of the sensing circuit at programmed intervals. According to various embodiments, impedance of the sensing circuit is measured at a frequency from 1 kHz to 1 MHz. According to one embodiment, a current pulse is generated at 20 Hz. The impedance of the sensing circuit is measured once every 30 seconds, in an embodiment. FIG. 3 illustrates a graphical diagram of measured impedance in a system for sensing magnetic fields, according to one embodiment. As shown in the drawing, the point at which the inductor's magnetic core saturates is when the voltage (for a given current) across the sensing circuit decreases significantly.

Implantable Medical Devices

Figure 4:
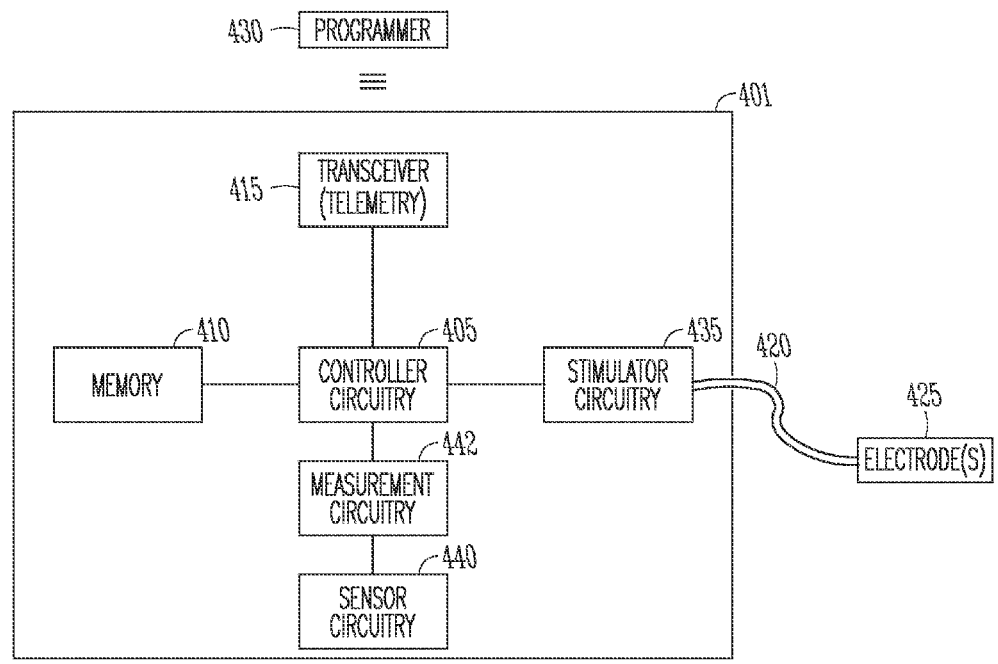
FIG. 4 illustrates a block diagram of a system with an IMD including a system for sensing magnetic fields, according to one embodiment.

FIG. 4 illustrates a block diagram of a system with an IMD including a system for sensing magnetic fields, according to one embodiment. The system includes an implantable medical device (IMD) 401, an electrical lead 420 coupled to the IMD 401, and at least one electrode 125. The IMD includes a controller circuit 405, a memory circuit 410, a telemetry circuit 415, and a stimulation circuit 435. The controller circuit 405 is operable on instructions stored in the memory circuit to deliver an electrical stimulation therapy. Therapy is delivered by the stimulation circuit 435 through the lead 420 and the electrode(s) 425. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. The illustrated system also includes sensor circuitry 440 with at least one inductor having a magnetic core that saturates in the presence of a magnetic field having a prescribed flux density. The device embodiment also includes an impedance measuring circuit 442 connected to the sensing circuit, the impedance measuring circuit adapted to measure the impedance of the sensing circuit and to provide a signal when the impedance changes by a prescribed amount. The controller circuit 405 is adapted to receive the signal and modify device behavior while in the presence of the magnetic field, according to various embodiments. According to various embodiments, the IMD 401 senses a magnetic field using the sensing circuit, measures the impedance of the sensing circuit using the measurement circuit, and sends a signal using the controller when the measured impedance indicates the inductor is saturated, as disclosed in the method depicted in FIG. 6, described below. While the sensor and measurement circuitry are shown within the device, either or both of them may be located outside the MID without departing from the scope of the disclosure.

According to various embodiments, the impedance measuring circuit includes a transthoracic impedance measurement module (TIMM). The sensing circuit includes a resistor-inductor-capacitor (RLC) circuit, according to various embodiments. In an embodiment, the sensing circuit includes multiple inductors oriented in more than one direction. The prescribed flux density includes flux density of a Magnetic Resonance Imaging (MRI) machine, according to one embodiment. According to various embodiments, the disclosed systems and methods can be used with a leadless device. For example, in an embodiment, one or more satellite electrodes are controlled wirelessly to deliver electrical therapy.

Figure 5:
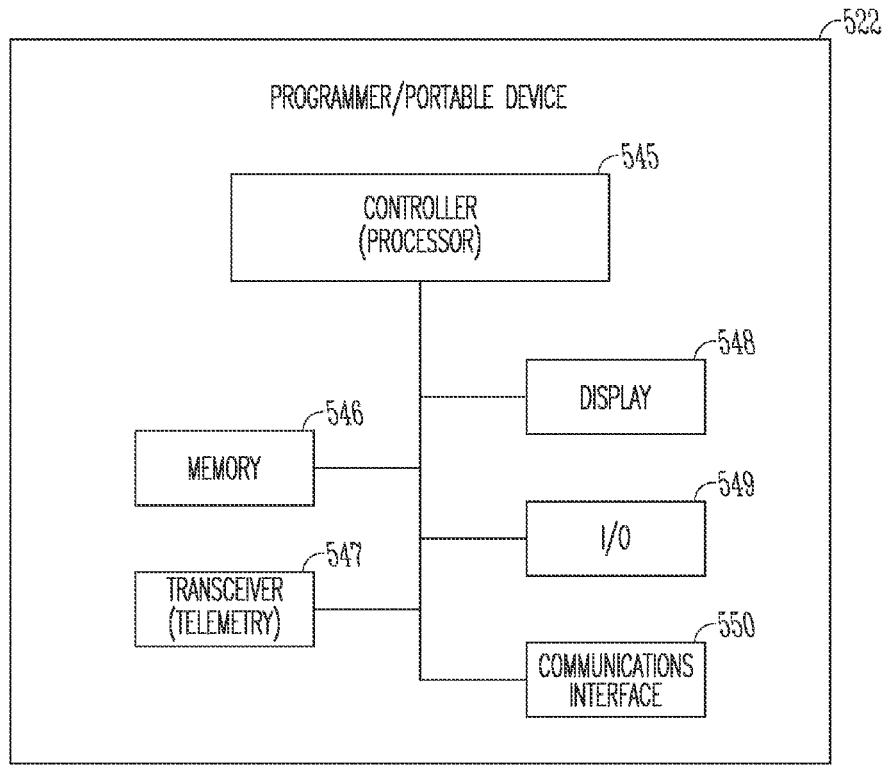
FIG. 5 illustrates a block diagram of a programmer such as illustrated in the system of FIG. 4 or other external device to communicate with the IMD(s), according to one embodiment.

FIG. 5 illustrates a programmer 522, such as the programmer 430 illustrated in the system of FIG. 4 or other external device to communicate with the implantable medical device(s), according to one embodiment. Examples of other external devices include Personal Digital Assistants (PDAs), personal laptop and desktop computers in an Advanced Patient Management (APM) system, or a handheld device such as an Advance Partner system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Methods for Sensing External Magnetic Fields

Figure 6:
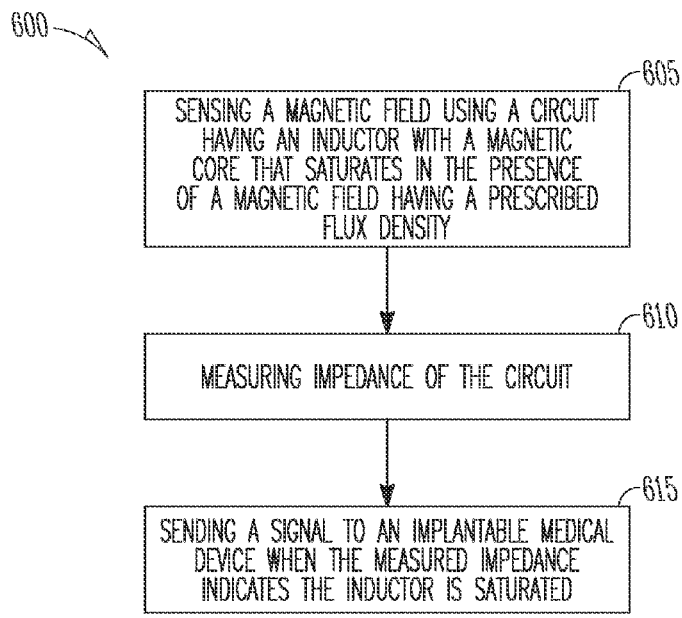
FIG. 6 illustrates a flow diagram of a method for sensing external magnetic fields from an IMD, according to one embodiment.

FIG. 6 illustrates a flow diagram of a method for sensing external magnetic fields from an MID, according to one embodiment. The method 600 embodiment includes sensing a magnetic field using a circuit having an inductor with a magnetic core that saturates in the presence of a magnetic field having a prescribed flux density, at 605. The method embodiment also includes measuring impedance of the circuit, at 610, and sending a signal to an implantable medical device when the measured impedance indicates the inductor is saturated, at 615. According to various embodiments, the method further includes modifying behavior of the implantable medical device upon receipt of the signal. Modifying device behavior may include changing to a pacing mode, changing to a tachy mode, changing lead configuration, or changing to a protect mode, according to various embodiments. Other types of device behavior or characteristics may be changed or modified upon receipt of the signal without departing from the scope of this disclosure.

According to various embodiments, measuring impedance of the circuit includes measuring impedance of the circuit by providing a current pulse to the circuit and measuring voltage across the circuit. The impedance may also be measured by providing a known voltage across the circuit and measuring the current through the circuit. Other methods for measuring impedance of the circuit may be used without departing from the scope of this disclosure.

Methods for Making a Magnetic Field Sensor

Figure 7:
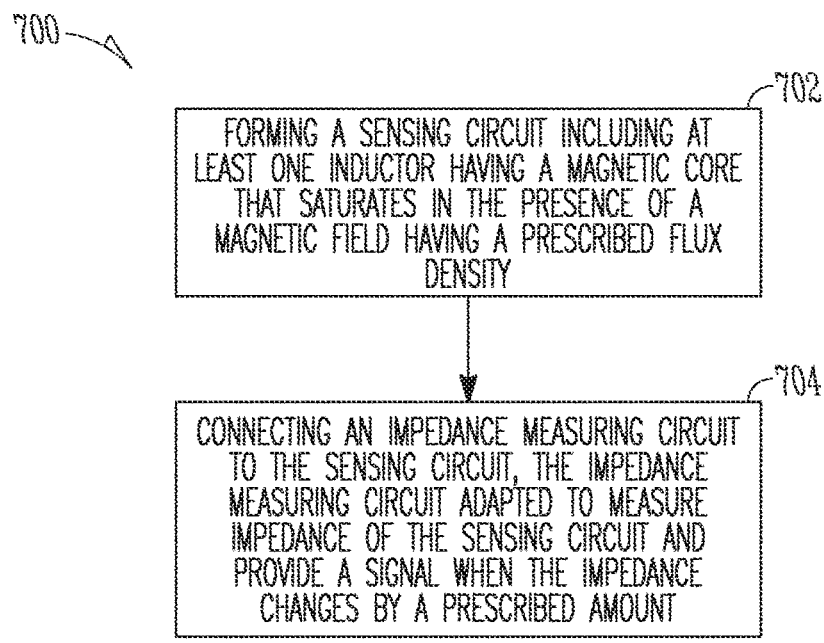
FIG. 7 illustrates a flow diagram of a method for making a magnetic field sensor, according to one embodiment.

FIG. 7 illustrates a flow diagram of a method for making a magnetic field sensor, according to one embodiment. An embodiment of the method 700 includes forming a sensing circuit, at 702. According to various embodiments, forming a sensing circuit includes forming a circuit with at least one inductor having a magnetic core that saturates in the presence of a magnetic field having a prescribed flux density. According to an embodiment, the prescribed flux density is that of an MRI device. The method embodiment also includes connecting an impedance measuring circuit to the sensing circuit, at 704. According to various embodiments, the impedance measuring circuit is adapted to measure impedance of the sensing circuit and provide a signal when the impedance changes by a prescribed amount. In one embodiment, the method also includes connecting a controller to the impedance measuring circuit, the controller adapted to receive the signal and modify behavior of an implantable medical device while in the presence of the magnetic field. The controller may modify device behavior to protect the device from damage due to the presence of the magnetic field, in various embodiments.

The present disclosure provides systems and methods for sensing external magnetic fields in implantable medical devices. The systems function as an omnidirectional MRI detection circuit capable of signaling the IMD to indicate the presence of a strong magnetic field. The described systems and methods have several advantages, including but not limited to: eliminating false charge timeouts that occur in devices when attempting to charge while magnetics are saturated; preventing induced currents from flowing in a lead system; and, as mentioned above, allowing an implantable device to modify its behavior when exposed to strong magnetic fields. The described systems and methods can be implemented as part of an implantable device, or separate from and in conjunction with the device. Types of devices that can benefit from the described systems and methods include, but are not limited to: cardiac resynchronization therapy (CRT) devices, defibrillators, pacemakers and neural stimulators.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An omnidirectional magnetic resonance imaging (MRI) detection apparatus to communicate a presence of an MRI device to an implantable medical device (IMD), the apparatus comprising:
    a sensing circuit including multiple inductors, each of the multiple inductors oriented in a different direction and having a magnetic core that saturates in the presence of a magnetic field having a flux density of the MRI device independent of direction, wherein sensing circuit is sized to fit within a housing of the IMD; and
    a control module connected to the sensing circuit, the control module adapted to monitor the inductors and to send a signal to the IMD when at least one of the inductors saturates.

2. The apparatus of claim 1, wherein the control module is configured to measure impedance of a circuit including the inductor.

3. The apparatus of claim 2, wherein the control module is adapted to measure impedance of a circuit including the inductor at a frequency from 1 kHz to 1 MHz.

4. The apparatus of claim 2, wherein the control module is adapted to measure impedance of a circuit including the inductor at a frequency of 20 Hz.

5. The apparatus of claim 2, wherein the control module is adapted to measure impedance of a circuit including the inductor once every 30 seconds.

6. The apparatus of claim 1, wherein one or more of the inductors includes a ferrite drum core inductor.

7. The apparatus of claim 1, wherein one or more of the inductors includes a gapped toroidal inductor.

8. The apparatus of claim 1, wherein one or more of the inductors includes a tape wound core inductor.

9. The apparatus of claim 1, wherein one or more of the inductors includes an isotropic material.

10. The apparatus of claim 1, wherein one or more of the inductors has maximum dimensions of 0.4 inches in width, 0.4 inches in length and 0.3 inches in height.

11. The apparatus of claim 1, wherein the control module includes a transthoracic impedance measurement module (TIMM) electrically connected to one or more of the inductors, the TIMM configured to measure impedance of a circuit including the inductor.

12. The apparatus of claim 11, wherein the apparatus is implantable.

13. The apparatus of claim 11, wherein the 1 MB is configured to change a lead configuration in response to the signal.

14. The apparatus of claim 11, wherein the control module is configured to change the IMD to a pacing mode in response to the signal.

15. The apparatus of claim 11, wherein the control module is configured to change the IMD to a tachy mode in response to the signal.

16. The apparatus of claim 11, wherein the control module is configured to change the IMD to a protect mode in response to the signal.

17. The apparatus of claim 11, wherein the IMD includes a cardiac resynchronization therapy (CRT) device.

18. The apparatus of claim 11, wherein the IMD includes a defibrillator.

19. The apparatus of claim 11, wherein the IMD includes a neural stimulator.

* * * * *